(12) United States Patent
Yan et al.

(10) Patent No.: US 9,165,042 B2
(45) Date of Patent: Oct. 20, 2015

(54) SYSTEM AND METHOD FOR EFFICIENTLY PERFORMING SIMILARITY SEARCHES OF STRUCTURAL DATA

(75) Inventors: Xifeng Yan, Urbana, IL (US); Philip Shilung Yu, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 1167 days.

(21) Appl. No.: 11/096,165

(22) Filed: Mar. 31, 2005

(65) Prior Publication Data
US 2006/0224562 A1    Oct. 5, 2006

(51) Int. Cl.
*G06F 7/00* (2006.01)
*G06F 17/30* (2006.01)
*G06F 19/00* (2011.01)

(52) U.S. Cl.
CPC ........ *G06F 17/30536* (2013.01); *G06F 19/705* (2013.01)

(58) Field of Classification Search
None
See application file for complete search history.

(56) References Cited

U.S. PATENT DOCUMENTS

| 6,502,105 | B1 * | 12/2002 | Yan et al. ............... 707/999.104 |
| 6,871,186 | B1 * | 3/2005 | Tuzhilin et al. .................... 707/1 |
| 7,624,337 | B2 * | 11/2009 | Sull et al. ....................... 715/201 |
| 2006/0116974 | A1 * | 6/2006 | Ashworth et al. ................. 707/1 |

OTHER PUBLICATIONS

Shasha et al., Algorithmics and Applications of Tree and Graph Searching, Proceedings of the twenty-first ACM SIGMOD-SIGACT-SIGART symposium on Principles of database systems, pp. 39-52, 2002.*
Abolmaali et al., The Compressed Feature Matrix—a novel descriptor for adaptive similarity search, Journal of Molecular Modeling, Springer Berlin, vol. 9, No. 1, pp. 66-75, Feb. 2003.*
Bunke et al., On the Minimum Common Supergraph of Two Graphs, Computing, ACM, vol. 65, Issue 1, pp. 13-25, 2000.*
D.S. Hochbaum, "Approximation Algorithms for NP-hand Problems," PWS Publishing Co., Boston, MA. pp. 135-143, (1996).
E.Ukkonen, "Approximate string-matching with q-grams and maximal matches," Theoretical Computer Science 92, pp. 191-211, (1992).
B. T. Messmer, et al, "Efficient Subgraph Isomorphism Detection: A Decomposition Approach," IEEE Transactions on Knowledge and Data Engineering, vol. 12, No. 2, Mar./Apr. 2000.
J.W. Raymond, et al, "RASCAL: Calculation of Graph Similarity using Maximum Common Edge Subgraphs," British Computer Society, The Computer Journal, vol. 45, No. 6, (2002).
X. Yan, et al., "Graph Indexing: A Frequent Structure-based Approach," SIGMOD 2004, Paris, France, Jun. 13-18, 2004.
T.R. Hagadone, "Molecular Substructure Similarity Searching: Efficient Retrieval in Two-Dimensional Structure Databases," The Upjohn Company, Kalamazoo, Michigan, pp. 515-521, Apr. 1992.
D. Shasha et al., "Algorithmics and Applications of Tree and Graph Searching," ACM Press, New York, NY (2002).
N. Nilson, "Principles of Artificial Intelligence," Tigoa Publishing Co., Palo Alto, California (1980).

* cited by examiner

*Primary Examiner* — Jau-Shya Meng
(74) *Attorney, Agent, or Firm* — Ryan, Mason & Lewis, LLP

(57) ABSTRACT

Techniques for similarity searching are provided. Structural data in a database is searched against one or more structural queries. A desired minimum degree of similarity between the one or more queries and the structural data in the database is first specified. One or more indices are then used to exclude from consideration any structural data in the database that does not share the minimum degree of similarity with one or more of the queries.

20 Claims, 10 Drawing Sheets

200

300

FIG. 4
400
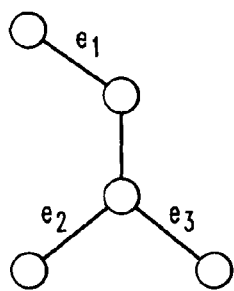
FIG. 5
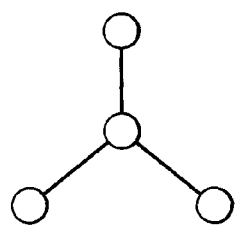   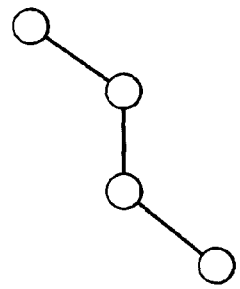   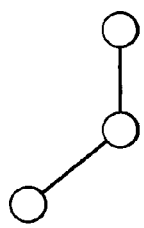
(a) $f_a$              (b) $f_b$              (c) $f_c$
FIG. 6
600
|     | $G_1$ | $G_2$ | $G_3$ | $G_4$ |
|-----|-------|-------|-------|-------|
| $f_a$ | 0 | 1 | 0 | 0 |
| $f_b$ | 0 | 0 | 1 | 0 |
| $f_c$ | 2 | 3 | 4 | 4 |

FIG. 7
700

|  | $f_a$ | $f_{b(1)}$ | $f_{b(2)}$ | $f_{c(1)}$ | $f_{c(2)}$ | $f_{c(3)}$ | $f_{c(4)}$ |
|---|---|---|---|---|---|---|---|
| $e_1$ | 0 | 1 | 1 | 1 | 0 | 0 | 0 |
| $e_2$ | 1 | 1 | 0 | 0 | 1 | 0 | 1 |
| $e_3$ | 1 | 0 | 1 | 0 | 0 | 1 | 1 |

GreedyCover

Input: Edge-feature Matrix $M$,
Maximum edge relaxations $k$.
Output: The number of feature misses $W_{greedy}$.

1: let $W_{greedy} = 0$;
2: for each $l = 1...k$ do
3:    select row $r_l$ that maximizes $|M(r_l, \cdot)|$;
4:    $W_{greedy} = W_{greedy} + |M(r_l, \cdot)|$;
5:    for each column c s.t. $M(r_l, c) = 1$ do
6:       set $M(\cdot, c) = 0$;
7: return $W_{greedy}$;

FIG. 9

$W_{est}(M, k, h, b)$

Input: Edge-feature Matrix $M$,
Number of edge relaxations $k$,
$h$ selection steps and $b$ disqualifying steps.
Output: Maximum feature misses $W_{est}$.

1:     if $b \geq B$ or $h \geq H$ then
2:          return $W_{apx}(M, k)$;
3:     select row $r_l$ that maximizes $|M(r_l, \cdot)|$;
4:     let $M' = M$ and $M'' = M$;
5:     set $M'(r_l, \cdot)=0$ and $M'(\cdot, c)=0$ for any $c$ if $M(r_l, c) = 1$;
6:     set $M''(r_l, \cdot)=0$;
7:     $W_1 = |M(r_l, \cdot)| + W_{est}(M', k, h + 1, b)$;
8:     $W_2 = W_{est}(M'', k, h, b + 1)$;
9:     $W_a = \max(W_1, W_2)$;
10:    $W_b = W_{apx}(M, k)$;
11:    return $\min(W_a, W_b)$;

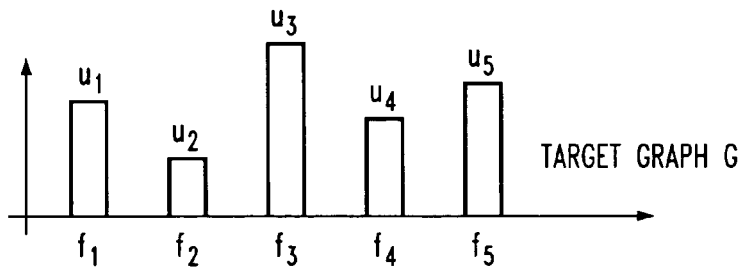

FIG. 10A

TARGET GRAPH G

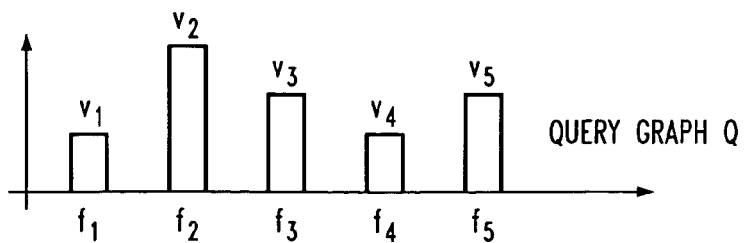

FIG. 10B

QUERY GRAPH Q

FIG. 11

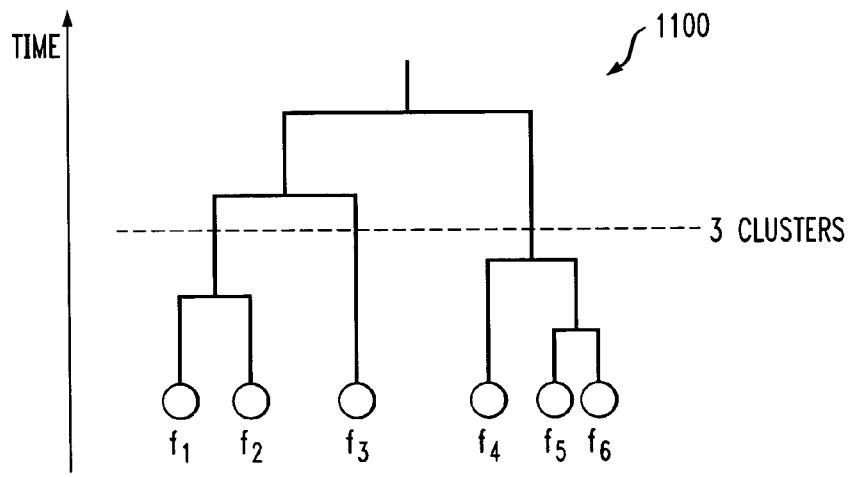

FIG. 12

```
                    GRAPH SIMILARITY FILTERING
Input:  Graph database D, Feature set F,
        Maximum feature size maxL, and
        A relaxed query Q.
Output: Candidate answer set C_Q.

1:   let C_Q = D;
2:   for each feature set F_i, i ≤ maxL do
3:        calculate the maximum feature misses d_max;
4:        C_Q = {G|d(G, Q) ≤ d_max, G ∈ C_Q};
5:   for each feature set F_i ∪ F_{i+1}, i < maxL do
6:        compute the selectivity based on C_Q;
7:        do the hierarchical clustering on features in F_i ∪ F_{i+1};
8:        cluster features into three groups, X_1, X_2, and X_3;
9:        for each cluster X_i do
10:            calculate the maximum feature misses d_max;
11:            C_Q = {G|d(G, Q) ≤ d_max, G ∈ C_Q};
12:  return C_Q;
```

SYSTEM AND METHOD FOR EFFICIENTLY PERFORMING SIMILARITY SEARCHES OF STRUCTURAL DATA

STATEMENT OF GOVERNMENT RIGHTS

This invention was made with Government support under Contract No.: Distillery TIA No. H98230-04-3-0001 awarded by the U.S. Department of Defense. The Government has certain rights in this invention.

FIELD OF THE INVENTION

The present invention relates to searching databases and, more particularly, to similarity searching in structural databases.

BACKGROUND OF THE INVENTION

Advanced database system research faces a great challenge necessitated by the emergence of massive, complex structural data (e.g., sequences, lattices, trees, graphs and networks) which are encountered in applications such as bio-informatics, geo-informatics and chem-informatics. A particular challenge involves efficiently and accurately searching databases of such structural data.

Graphs are the most general form of structural data, and thus are used extensively in chem-informatics and bio-informatics datasets. For example, graph-structured databases have been used heavily in the development of chemical structure search and registration systems. Graph-structured databases are also being used in computer vision and pattern recognition, wherein graphs are used to represent complex structures, such as hand-drawn symbols, three-dimensional objects and medical images.

A number of methods have been developed to handle data queries involving complex structural data. See, for example, S. Beretti et al., *Efficient Matching and Indexing of Graph Models in Content Based Retrieval*, 23 IEEE TRANS. ON PATTERN ANALYSIS AND MACHINE INTELLIGENCE, pgs. 1089-1105 (2001); D. Shasha et al., *Algorithmics and Applications of Tree and Graph Searching*, IN PROC. 21st ACM SYMP. ON PRINCIPLES OF DATABASE SYSTEMS (PODS'02), pgs. 39-52 (2002) (hereinafter "Shasha"); X. Yan et al., *Graph Indexing: A Frequent Structure-Based Approach*, IN PROC. 2004 ACM INT. CONF. ON MANAGEMENT OF DATA (SIGMOD'04), pgs. 335-346 (2004) (hereinafter "Yan"); J. Raymond et al., *Rascal: Calculation of Graph Similarity Using Maximum Common Edge Subgraphs*, 45 THE COMPUTER JOURNAL, pgs. 631-644 (2002) (hereinafter "Raymond"); and N. Nilsson, *Principles of Artificial Intelligence*, Morgan Kaufmann, Palo Alto, Calif., (1980) (hereinafter "Nilsson"), the disclosures of which are incorporated by reference herein.

While these methods are very useful, they do have important limitations. Specifically, none of the cited methods accommodate searching databases of structural data against a query structure to find structures in the database that are similar, but not exactly the same as, a portion or portions of the query. As a result, highly relevant structures in the database inevitably will be overlooked.

Therefore, improved techniques for similarity searching databases of structural data would be desirable.

SUMMARY OF THE INVENTION

Techniques for similarity searching are provided. In one aspect of the invention, a method of searching structural data in a database against one or more structural queries comprises the following steps. A desired minimum degree of similarity between the one or more queries and the structural data in the database is first specified. One or more indices are then used to exclude from consideration any structural data in the database that does not share the minimum degree of similarity with one or more of the queries.

A more complete understanding of the present invention, as well as further features and advantages of the present invention, will be obtained by reference to the following detailed description and drawings.

BRIEF DESCRIPTION OF THE DRAWINGS

FIG. 4 is a diagram illustrating an exemplary query graph according to an embodiment of the present invention;

FIG. 5 is a diagram illustrating three structural fragments, $f_a$, $f_b$ and $f_c$, according to an embodiment of the present invention;

FIG. 6 is a diagram illustrating an exemplary feature-graph matrix index according to an embodiment of the present invention;

FIG. 7 is a diagram illustrating an exemplary edge-feature matrix index according to an embodiment of the present invention;

FIG. 8 is a diagram illustrating an exemplary greedy methodology for determining a maximal number of feature misses according to an embodiment of the present invention;

FIG. 9 is a diagram illustrating another exemplary methodology for determining a maximal number of feature misses according to an embodiment of the present invention;

FIGS. 10A-B are diagrams illustrating exemplary feature vectors according to an embodiment of the present invention;

FIG. 11 is a diagram illustrating a hierarchical clustering tree according to an embodiment of the present invention;

FIG. 12 is a diagram illustrating an exemplary methodology for graph similarity filtering according to an embodiment of the present invention;

DETAILED DESCRIPTION OF PREFERRED EMBODIMENTS

Figure 1:
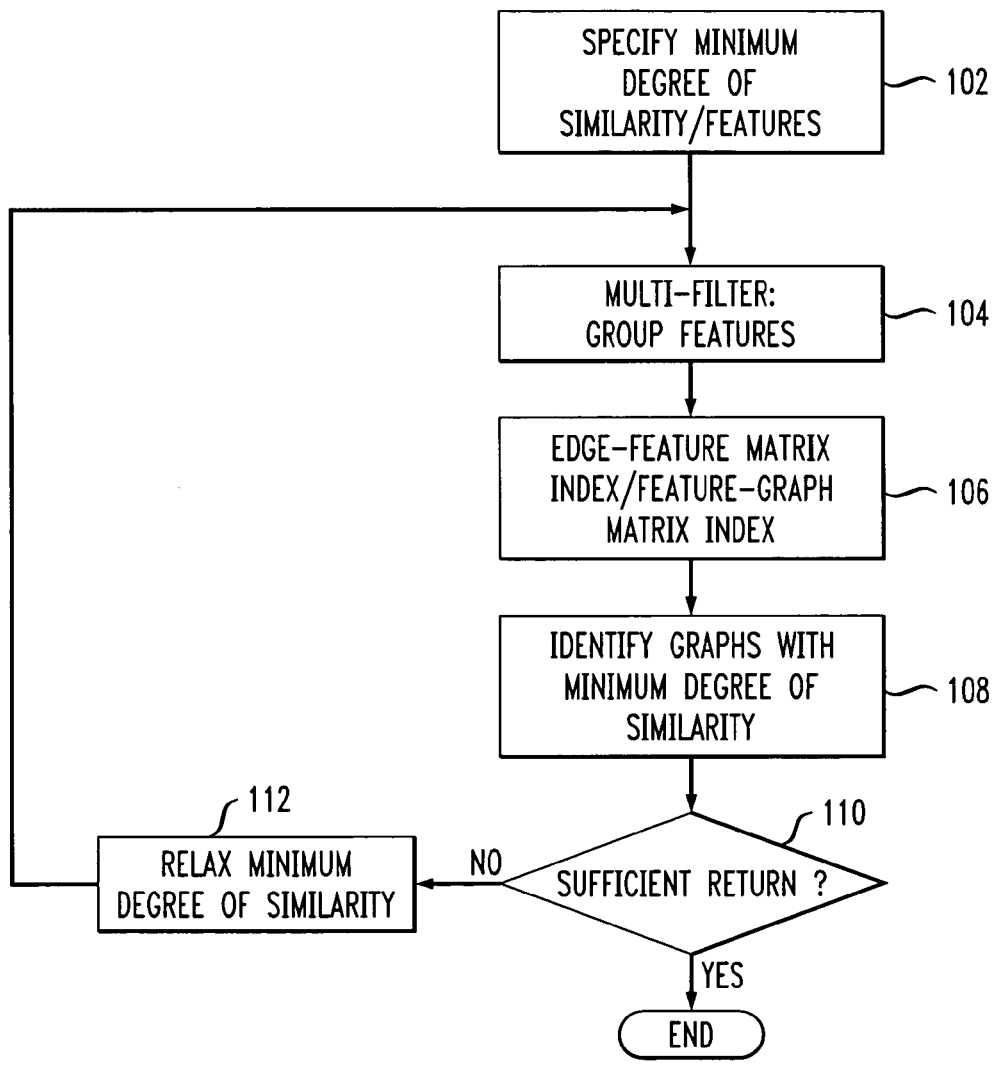
FIG. 1 is a diagram illustrating an exemplary methodology for searching graphs in a database according to an embodiment of the present invention.

FIG. 1 is a diagram illustrating exemplary methodology 100 for searching graphs in a database. Specifically, methodology 100 may be employed to search graphs in a database against one or more query graphs. The term "graph," as used herein, is intended to include, but not be limited to, any form of structural data comprising one or more features, such as, graph data sets, images, sequences and combinations comprising at least one of the foregoing data forms.

In step 102, a minimum degree of similarity between the query graph(s) and the graphs in the database is specified. As will be described in detail below, the minimum degree of similarity may be based, at least in part, on one or more features present in the query graph and the graphs in the database. By way of example only, suitable features, e.g., for basing graph similarity, include, but are not limited to, structures indexed in structural, e.g., graph, databases, paths, edges, discriminative frequent substructures, elementary substructures and combinations comprising at least one of the foregoing features.

In step 104, a multi-filter approach may be used to group features with similar selectivity or similar sizes. The multi-filter approach will be described in detail below. This will aid in excluding from consideration any graphs in the database that do not share the desired minimum degree of similarity with the query graph. See description of step 106, below.

In step 106, an edge-feature matrix index and/or a feature-graph matrix index may be used to exclude from consideration any graphs in the database that do not share the desired minimum degree of similarity with the query graph. As will be described in detail below, the feature-graph matrix index represents the number of feature differences between the query graph and the graphs in the database. As will also be described in detail below, the edge-feature matrix index represents a limit on the minimum number of features in common between the query graph and the graphs in the database, based on a relaxation ratio of the query. The relaxation ratio is also defined below.

In step 108, graphs, or a substructure(s) thereof, in the database are identified that share at least the desired minimum degree of similarity with at least a portion of the query graph. The term "substructure," or the term "subgraph," as used herein, denote any subset or fragment of a graph. Identifying graphs in the database will be described in detail below.

In step 110, it is determined whether or not a sufficient number of matching graphs are returned. If the number is sufficient, then methodology 100 ends. If, however, the number of graphs returned is insufficient, the minimum degree of similarity parameter can be altered and steps 104-110 may be repeated. See step 112 below.

In step 112, the minimum degree of similarity parameter may be altered, e.g., to potentially change the number of matches with the query graph in the database. For example, if the minimum degree of similarity parameter is relaxed it may increase the number of matches with the query graph. Altering the minimum degree of similarity parameter will be described in detail below.

Figure 2:
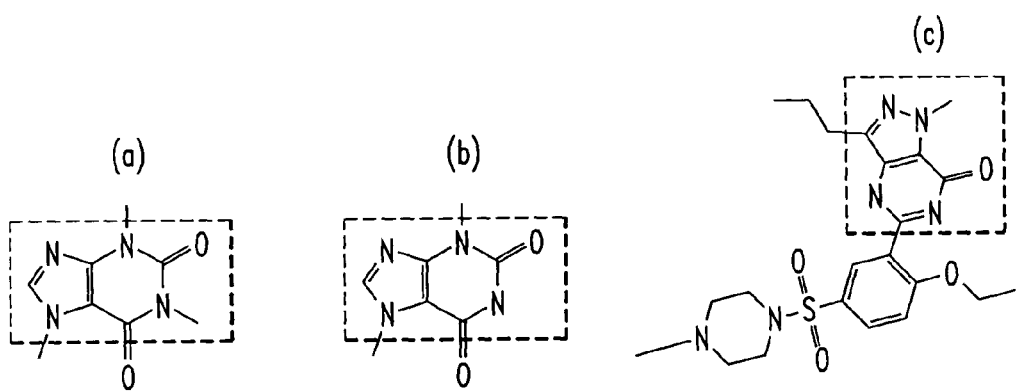
FIG. 2 is a diagram illustrating an exemplary database of chemical structures according to an embodiment of the present invention.
Figure 3:
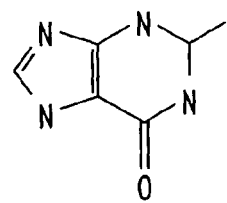
FIG. 3 is a diagram illustrating an exemplary chemical structure query according to an embodiment of the present invention.

By way of example only, FIG. 2 is a diagram illustrating an exemplary database 200 of chemical structures. Exemplary database 200 comprises three chemical structures, structure (a): caffeine, structure (b): thesal and structure (c): Viagra™. FIG. 3 is a diagram illustrating exemplary chemical structure query 300.

If one were to search for exact instances of query graph 300 of FIG. 3 in database 200 (FIG. 2), no matches would be returned. However, according to the present techniques, the search criteria can be relaxed so that structures similar to query graph 300 may be found.

The degree of similarity, as described, for example, in conjunction with the description of step 102 of FIG. 1, above, may be a function of the number of features query graph 300 shares with one or more graphs in database 200. For example, if the degree of similarity is defined to include graphs having all but one edge in common with query graph 300, then matches with structures (a) and (b) in database 200 would be returned. Therefore, query graph 300 comprises a substructure of both structures (a) and (b) in database 200, as indicated by the dashed boxes, with all but one edge in common.

It should be noted that, as is the case in FIGS. 2 and 3, the one missing edge is the same in both cases. However, according to the teachings presented herein, the missing edge can be different, and a match will result, as long as the number of missing edges does not exceed a certain threshold number. However, as will be described in detail below, constraints may be placed on which edges may be missed.

If the degree of similarity is further defined to include graphs having all but two edges in common, then matches of query graph 300 with structures (a): caffeine, (b): thesal and (c): Viagra™ in database 200 would be returned. Specifically, query graph 300, as mentioned above, comprises a substructure of both structures (a) and (b) in database 200 with all but one edge in common. Further relaxing the degree of similarity also results in structure (c) being a match, as indicated by the dashed box.

Use of conventional techniques to perform the above similarity searches would not be viable. For example, deleting one or more edges from a query and then using conventional pair-wise substructure similarity comparison to find exact matches with the query would return an insurmountable number of matches, many of which would be undesirable.

For example, if the degree of similarity was defined to include any graph in the database possessing all but three edges in common with a 20 edge query graph, then about $$\binom{20}{3} = 1140$$

different query graphs would have to be searched to exhaust all possible combinations missing exactly three edges of the query. Searching this way would be impractical.

According to one exemplary embodiment, as will be described in detail below, feature-based structural filtering methodologies, e.g., graph similarity filtering techniques, are used to efficiently filter graphs in a large scale graph database. Graph similarity filtering functions by querying graphs as a set of features and transforming the edge deletions into the feature misses in the query graph. With a limit on the minimum number of features in common, graph similarity filtering can filter many graphs from a database directly, without performing pair-wise similarity computation.

To facilitate the feature-based filtering, as mentioned, for example, in conjunction with the description of step 106 of FIG. 1, above, two data structures are introduced, a feature-graph matrix and an edge-feature matrix. The feature-graph matrix is an index structure used to compute differences in the numbers of features between a query graph and the one or more graphs in a database. The edge-feature matrix is an index that is built "on-the-fly" to compute a limit on the minimum number of features in common between the query graph and the one or more graphs in the database, based on a query relaxation ratio.

As mentioned, for example, in conjunction with the description of step 104 of FIG. 1, above, a multi-filter composition strategy is disclosed herein, wherein each of a multiple of filters uses distinct and complimentary subsets of the features of the graph, e.g., to group features with similar selectivity. A multi-filter composition strategy can improve performance significantly for a moderate relaxation ratio, e.g., between about ten and 20 percent, defined below. The filters are constructed by a hierarchical, one dimensional, clustering methodology that groups features with similar selectivity into a single feature set. For example, a feature shared by about one percent of the features in a database would be considered a highly selective feature.

The use of feature-based filtering methodologies can provide for efficient substructure similarity searching. Moreover, the techniques presented herein can be applied to searching approximate, non-consecutive sequences, trees, and other complicated structures as well.

For ease of reference, the remainder of the detailed description will be divided into the following sections: (I) Preliminary Concepts, (II) Structural Filtering, (III) Feature Set Selection, (IV) Methodology Implementation and (V) Empirical Study.

(I) Preliminary Concepts

Graphs are widely used to represent complex structures that are difficult to model. Several different types of graphs exist. One type, called a labeled graph, has vertices and edges that are associated with attributes, typically labeled s. Another type, called an unlabeled graph, has vertices and edges, but no attributes associated with them. Some exemplary attributes include, but are not limited to, tags in extensible markup language (XML) documents, atoms/bonds in chemical compounds, genes in biological networks and object descriptors in images.

The use of labeled graphs or unlabeled graphs depends on the application. The techniques presented herein are applicable to both labeled graphs and unlabeled graphs.

The parameters of a graph may be defined as follows. The vertex set of a graph G may be denoted by V(G) and the two edge set by E(G). A label function l maps a vertex or an edge to a label. The size of a graph is defined by the number of edges it has, written as |G|.

Further, a graph G is a subgraph of graph G' if there exists a subgraph isomorphism from G to G', denoted by $G \subseteq G'$. In this case G' is called a supergraph of G.

A subgraph isomorphism is an injective function $f: V(G) \rightarrow V(G')$, such that (1) $\forall u \in V(G), l(u)=l'(f(u))$ and (2) $\forall (u,u) \in E(G), (f(u),f(v)) \in E(G')$ and $l(u,v)=l'(f(u),f(v))$, wherein l and l' are the label functions of G and G', respectively. $f$ is called an embedding of G in G'.

Substructure similarity searching may involve at least two scenarios, similarity searching and reverse similarity searching. Similarity searching may be defined as follows. For a graph database $D=\{G_1, G_2, \ldots, G_n\}$ and a query graph Q, a similarity search may be conducted to discover all the graphs that approximately contain query graph Q. Reverse similarity searching may be defined as follows. For a graph database $D=\{G_1, G_2, \ldots, G_n\}$ and a query graph Q, a reverse similarity search may be conducted to discover all the graphs in the database that are approximately contained by query graph Q. By way of example only, a similarity search may be conducted to discover all graphs that contain greater than or equal to about 90 percent of query graph Q. See, for example, FIGS. 2 and 3, described above.

Each type of search scenario, similarity searching and reverse similarity searching, has its own applications. In chem-informatics, for example, similarity searching is more popular. Reverse similarity searching, on the other hand, has key applications in pattern recognition. While the techniques presented herein are primarily directed to similarity searching, they may easily be adapted, by one of ordinary skill in the art, to apply to reverse similarity searching.

To distinguish a query graph from the graphs in a database, the graphs in the database may be called "target graphs." As such, the present techniques address measuring substructure similarity between target graphs and a query graph.

Several similarity measures are identified herein and are grouped into three distinct categories. The first category involves physical property-based measures, such as, toxicity and weight. The second category involves feature-based measures. The third category involves structure-based measures.

For the feature-based measures, domain-specific elementary structures are first extracted as features. Whether two graphs are similar is determined by the number of common elementary structures they have. For example, two compounds can be compared based on the number of benzene rings they each have.

Under this similarity definition, each graph is represented as a feature vector, $x=[x_1, x_2, \ldots x_n]^T$, wherein $x_i$ is the frequency of feature $f_i$. The distance between two graphs is measured by the distance between their feature vectors. The feature-based approach, however, only provides a very rough measure of structural similarity since it loses the global structural connectivity, or the overall relationship of features to one another. Specifically, two graphs may share one or more of the same features but, in fact, may not be relevantly related.

In contrast, structure-based similarity measures directly compare the topology of two graphs, which is often costly to compute. However, since these measures take structural connectivity fully into consideration, they are more accurate than the feature-based measures. Specifically, with structure-based similarity measures, the maximum common subgraph is used to measure the full structure similarity.

No matter what the definition used is, the matching of two graphs can be regarded as a result of three editing operations, namely, insertion, deletion and re-labeling. According to substructure similarity searching, each of these operations relaxes the query graph by deleting or re-labeling one edge (insertion does not change the query graph). Without loss of generality, the percentage of maximum retained edges in the query graph is taken as a similarity measure.

A parameter called the relaxation ratio may be defined as follows: Given two graphs G and Q, if P is the maximum common subgraph of G and Q, then the substructure similarity between G and Q is defined by $$\frac{|E(P)|}{|E(Q)|} \cdot 1 - \frac{|E(P)|}{|E(Q)|}$$

is called the relaxation ratio.

For example, with reference to structure (a): caffeine in database 200 (FIG. 2) and query graph 300 (FIG. 3), their maximum common subgraph (which is not necessarily connected) comprises eleven edges. Thus, the substructure similarity between these two graphs is around 92 percent with respect to the query graph (e.g., eleven of the twelve edges of query graph 300 may be found in structure (a)). This means that if the query graph is relaxed by eight percent, then structure (a) in database 200 contains the relaxed query graph. Note that the relaxation ratio is not symmetric. The similarity of structures (b) and (c) in database 200 with query graph 300 may also be similarly computed. Specifically, the similarity of structures (b) and (c) in database 200 with query graph 300 is 92 percent (one missed edge) and 67 percent (four missed edges), respectively.

In the present techniques, a connection is built between the structure-based measure and the feature-based measure so that the feature-based measure can be used to screen a database before performing pair-wise structure-based similarity computation. Using this strategy, the advantages of both measures, namely efficiency from the feature-based measure and accuracy from the structure-based measure, can be maximally exploited.

(II) Structural Filtering

As mentioned, for example, in conjunction with the description of step 106 of FIG. 1, above, any graphs in a database that do not share the desired minimum degree of similarity with the query graph are excluded from consideration, e.g., filtered out. Specifically, given a relaxed query graph, a goal of the present techniques is to filter as many graphs as possible using a feature-based approach. As mentioned above, the features discussed herein may comprise paths, edges, discriminative frequent structures, elementary structures, or any structures indexed in graph databases. For a discussion of paths, see, for example, Shasha, and for a discussion of discriminative frequent structures, see, for example, Yan. Previous works, however, did not investigate the connection between the structure-based similarity measure and the feature-based similarity measure. In the present techniques, the query relaxation ratio is explicitly transformed to the misses of indexed features, thus building a connection between a structure-based similarity measure and a feature-based similarity measure.

For example, FIG. 4 is a diagram illustrating an exemplary query graph 400 and FIG. 5 is a diagram illustrating three structural fragments, $f_a$, $f_b$ and $f_c$. Assume that these structural fragments are indexed as features in a graph database.

For simplicity, all the label information is ignored in this example. Therefore, the symbols $e_1$, $e_2$, and $e_3$, for example in FIG. 4, do not represent labels, but the edges themselves.

Suppose further that one cannot find any match for query graph 400 in a given graph database. One may then relax one edge, $e_1$, $e_2$, or $e_3$, through a deletion or re-labeling operation. The middle edge (not labeled) is preferably retained, because the deletion of that edge may break the query graph into pieces, which should be avoided.

Because the relaxation can take place among any one of $e_1$, $e_2$, and $e_3$, it is not certain which feature(s) will be affected by this relaxation. However, regardless of which edge is relaxed, the relaxed query graph should have at least three occurrences of these features. Equivalently, the relaxed query graph may miss at most four occurrences of these features, as compared to original query graph 400 (which has seven occurrences of these features, namely, one $f_a$, two $f_b$'s, and four $f_c$'s). Using this information, graphs can be discarded that do not contain at least three occurrences of these features. The above filtering concept is called feature-based structural filtering.

An index structure, the feature-graph matrix index, as mentioned, for example, in conjunction with the description of step 106 of FIG. 1, above, is now introduced to facilitate the feature-based filtering. Each column of the feature-graph matrix index corresponds to a target graph in the graph database, while each row of the feature-graph matrix index corresponds to a feature being indexed. Each entry records the number of the embeddings of a specific feature in a target graph. An exemplary feature-graph matrix index is shown, for example, in FIG. 6.

By way of example only, suppose a sample database has four graphs, $G_1$, $G_2$, $G_3$ and $G_4$. FIG. 6 shows exemplary feature-graph matrix index 600 based on that sample database. For instance, as shown in FIG. 6, $G_1$ has two embeddings of $f_c$.

The feature-graph matrix index is easily maintainable. Each time a new graph is added to the graph database, only an additional column needs to be added.

Using the feature-graph matrix index, feature-based filtering can be applied on any query graph against a target graph in the database using any subset of the indexed features. Consider query graph 400 (FIG. 4), with one edge relaxation. According to the feature-graph matrix index shown, for example, in FIG. 6, even if the structure of $G_1$ is not known, $G_1$ can be filtered immediately based on the features included in $G_1$. Specifically, $G_1$ can be filtered since it only contains two occurrences of $f_a$, $f_b$ and $f_c$.

This feature-based filtering process does not involve any time consuming structure similarity checking. The only computation needed is to retrieve the features from the index that belong to a particular query graph and compute the possible feature misses for a given relaxation ratio. Since the present filtering techniques are fully based on the feature-graph matrix index, the physical database does not have to be accessed unless calculating the accurate substructure similarity is desired.

The general framework of processing a similarity search and how it relates to the present structural filtering techniques will now be described. Given a graph database and a query graph, a substructure similarity search can be performed in the following four steps. The first step, the index construction step, involves selecting small structures as features in the graph database, and building the feature-graph matrix between the features and the graphs in the database.

The second step, the feature miss estimation step, involves determining the indexed features belonging to the query graph, selecting a feature set (i.e., a subset of the features), calculating the number of selected features contained in the query graph and then computing the upper bound of feature misses if the query graph is relaxed with one edge deletion or re-labeling. This upper bound is written $d_{max}$. Some portion of the query graph, e.g., key functional structures, can be specified as not to be altered, as completely arbitrary relaxations can lead to matches with less interest.

The third step, the query processing step, involves using the feature-graph matrix index to calculate a difference in the number of features between each graph G in the database and query Q. If the difference is greater than $d_{max}$, then the graph G is discarded. The graphs that remain constitute a candidate answer set, written as $C_Q$. False positives in $C_Q$ may be eliminated using conventional techniques. Substructure similarity is then calculated also using conventional techniques.

The fourth step, the query relaxation step, involves relaxing the query further if, for example, more matches are needed than are returned from the previous steps. In this instance, the second step (feature miss estimation step), the third step (query processing step) and the fourth step (query relaxation step) may be repeated, with further relaxation of the query, to potentially generate more matches.

The feature-graph matrix index in the first step (the index construction step) may be constructed prior to its use in the process, and can further be used for any query. The similarity search for a query graph takes place in the second step (feature miss estimation step) and the third step (query processing step). According to the instant techniques, it is preferred that the candidate answer set returned be as small as possible, since the cost of the accurate similarity computation is proportional to the size of the candidate set. A discussion of calculating pair-wise substructure similarity may be found, for example, in T. Hagadone, *Molecular Substructure Similarity Searching: Efficient Retrieval In Two-Dimensional Structure Databases*, 32 J. CHEM. INF. COMPUT. SCI., pgs. 515-521 (1992); Nilsson; and Raymond, the disclosures of which are incorporated by reference herein.

In the second step (feature miss estimation step), the number of features in the query graph is calculated. Because one feature may have multiple occurrences in a graph, the number of embeddings of features is used instead of the number of features. Thus, the two terms, "the number of features" and "the number of embeddings of features," are used synonymously herein.

Substructure similarity searching is akin to approximate string matching (string matching typically involves one-dimensional strings, such as the sequence a, b, c, d). In approximate string matching, filtering methodologies, such as q-gram, achieve the best performance because they do not inspect all the string characters. However, such filtering methodologies only work for moderate relaxation ratios and need a validation methodology to check the actual matches.

Similar arguments may also be made with regard to the structural filtering methodology in the present substructure similarity search. However, since the present techniques relate to substructure similarity searching, the relaxation ratios are moderate.

Feature miss estimation will now be described. A string with q characters is called a q-gram. A typical q-gram filtering methodology builds an index for all q-grams in a string database. A query string Q is broken into a set of q-grams, which are compared against the q-grams of each target string in the database. If the difference in the number of q-grams is greater than the following threshold, Q will not match this string within k edit distance.

Given two strings P and Q, if their edit distance is k, their difference in the number of q-grams is at most kq. See for example, E. Ukkonen, *Approximate String Matching With q-grams and Maximal Matches*, THEORETIC COMPUTER SCIENCE, pgs. 191-211 (1992), the disclosure of which is incorporated by reference herein. It may then be checked whether a bound for q-size substructures can be similarly derived. A succinct bound like the one given to q-grams, however, may not be drawn due to the following two issues. First, in substructure similarity searching, the space of q-size subgraphs is explosive (e.g., grows exponentially) with respect to q. This contrasts with the string case, wherein the number of q-grams in a string is linear to its length. Secondly, even if all of the q-size subgraphs are indexed, the above q-gram bound will not be valid since the graph does not have the linearity that the string does.

An edge-feature matrix is used to build a map between edges and features for a query graph. In this matrix, each row represents an edge while each column represents an embedding of a feature. FIG. 7 is a diagram illustrating exemplary edge-feature matrix index 700. Edge-feature matrix index 700 is constructed, for example, for query graph 400 (FIG. 4) and features (a), (b) and (c) (FIG. 5).

All of the embeddings of features are recorded in edge-feature matrix index 700. For example, the second and the third columns of edge-feature matrix index 700 are two embeddings of feature $f_b$ in the query graph. The first embedding of $f_b$ covers edges $e_1$ and $e_2$ while the second embedding covers edges $e_1$ and $e_3$. The middle edge does not appear in the edge-feature matrix, e.g., if a user prefers retaining it. An edge $e_i$ hits a feature $f_j$, if $f_j$ contains $e_i$.

It is not too time consuming to build the edge-feature matrix on-the-fly, since the features used are small simple structures. Specifically, in most cases, the structures have less than ten edges. See, for example, Shasha and Yan. Whenever an embedding of a feature is discovered, a new column is appended to the matrix.

The feature miss estimation problem can be stated as follows: Given a query graph Q and a set of features contained in Q, if the relaxation ratio is μ, what is the maximal number of features that can be missed? In fact, it is the maximum number of columns that can be hit by k rows in the edge-feature matrix, wherein $k = \lfloor \theta \cdot |G| \rfloor$. This is a maximum coverage (or set k-cover) problem, which has been proven NP-complete.

The optimal solution that finds the maximal number of feature misses can be approximated by a "greedy" methodology, which always takes the best immediate, or local, solution while finding an answer. The methodology first selects a row that hits the largest number of columns and then removes this row and the columns covering it. This selection and deletion operation is repeated until k rows are removed. The number of columns removed by this methodology provides a way to estimate the upper bound of feature misses.

FIG. 8 is a diagram illustrating exemplary greedy methodology 800 for determining a maximal number of feature misses. In FIG. 8, the loop including lines 1-7 of the pseudo code is an iterative process that provides a number of feature misses, $W_{greedy}$. In methodology 800, M(r,c) represents the entry in the $r^{th}$ row, $c^{th}$ column of matrix M. M(r,•) denotes the $r^{th}$ row vector of matrix M, while M(•,c) denotes the $c^{th}$ column vector of matrix M. |M(r,•)| represents the number of non-zero entries in M(r,•).

If $W_{greedy}$ and $W_{opt}$ are the total feature misses computed by the greedy solution and by the optimal solution, respectively, then, $$W_{greedy} \geq \left[1 - \left(1 - \frac{1}{k}\right)^k\right] W_{opt} \geq \left(1 - \frac{1}{e}\right) W_{opt}, \quad (1)$$

wherein k is the number of edge relaxations. See, for example, D. Hochbaum, *Approximation Algorithms for NP-Hard Problems*, PWS Publishing, MA (1997), the disclosure of which is incorporated by reference herein.

The optimal solution cannot be approximated in polynomial time within a ratio of (e/(e−1)+o(1)), unless P=NP. The inequality, presented above, can be rewritten as, $$W_{opt} \le \frac{1}{1-\left(1-\frac{1}{k}\right)^k} W_{greedy} \quad (2)$$

$$W_{opt} \le \frac{e}{e-1} W_{greedy}$$

$$W_{opt} \le 1.6 W_{greedy}.$$

Traditional applications of the maximum coverage problem focus on how to approximate the optimal solution as best as possible. The instant techniques, however, focus on the upper bound of the optimal solution. Let $\max_r |M(r,\bullet)|$ be the maximum number of features that one edge hits. Obviously, $W_{opt}$ should be less than k times this number, $$W_{opt} \le k \times \max_r |M(r;)|. \quad (3)$$

Estimation refinement will now be discussed. A tight bound of $W_{opt}$ is critical to the filtering performance. A tighter bound often leads to a smaller set of candidate graphs. Although the bound derived by methodology 800 cannot be further improved asymptotically, methodology 800 may still be improved for a tighter bound.

$W_{opt}(M,k)$ is the optimal value of the maximum feature misses for k edge relaxations. Suppose row $r_l$ maximizes $|M(r_l,\bullet)|$. Let M' be M except $M'(r_l,\bullet)=0$ and $M'(\bullet,c)=0$ for any column c that is hit by $r_l$, and M" be M except $M''(r_l,\bullet)=0$.

Any optimal solution that leads to $W_{opt}$ should be in the following two cases. In case 1, $r_l$ is selected in this solution, and in case 2 $r_l$ is not selected (e.g., $r_l$ is disqualified for the optimal solution).

In the first case, the optimal solution should also be the optimal solution for the remaining matrix M'. That is, $W_{opt}(M,k)=|M(r_l,\bullet)|+W_{opt}(M',k-1)$. k−1 means that the remaining k−1 rows need to be removed from M' since row $r_l$ is selected. In the second case, the optimal solution for M should be the optimal solution for M", i.e., $W_{opt}(M,k)=W_{opt}(M'',k)$. k means that k rows still need to be removed from M" since row $r_l$ is disqualified.

The first case is called the selection step, and the second case is called the disqualification step. Since the optimal solution is to find the maximum number of columns that are hit by k edges, $W_{opt}$ should be equal to the maximum value returned by these two steps. Therefore, the following conclusion can be drawn $$W_{opt}(M,k) = \max \begin{cases} |M(r_l;)| + W_{opt}(M',k-1), \\ W_{opt}(M'',k) \end{cases} \quad (4)$$

which suggests a recursive solution to calculating $W_{opt}$. This is equivalent to enumerating all the possible combinations of k rows in the edge-feature matrix index, which may be very time consuming. However, the top levels of this recursive process are of interest, especially for the case where most of the features intensively cover a set of common edges. For each matrix M' (or M") that is derived from the original matrix M after several recursive calls in Equation (4), M' encounters interleaved selection steps and disqualifying steps. Suppose M' has h selected rows and b disqualified rows. h is restricted to be less than H, and b is restricted to be less than B, wherein H and B are predefined constants. H+B should be less than the number of rows in the edge-feature matrix index. In this way, the depth of the recursion can be controlled.

$W_{apx}(M,k)$ is the upper bound of the maximum feature misses calculated using Equations (2) and (3), above, wherein M is the edge-feature matrix and k is the number of edge relaxations. The above discussion is formulated in the methodology shown in FIG. 9.

FIG. 9 is a diagram illustrating exemplary methodology 900 for determining a maximal number of feature misses. In FIG. 9, the loop including lines 1-11 of the code is an iterative process that provides a maximum number of feature misses, $W_{est}$. By way of example only, in line 7 of methodology 900, row $r_l$ is selected. In line 8 of methodology 900, row $r_l$ is disqualified. Lines 7 and 8 of methodology 900 correspond to the selection and disqualification steps shown in Equation (4). In line 9 of methodology 900 the maximum value of the result returned by lines 7 and 8 is calculated. Meanwhile, methodology 900, shown in FIG. 9, can be used to get the upper bound of $W_{opt}$ directly, as line 11 does.

Methodology 900 returns the best estimation of the bound that can be obtained. The condition in line 1 of methodology 900 will terminate the recursion when it selects H rows or when it disqualifies B rows. Methodology 900 is a classical branch-and-bound approach.

Parameters H and B are selected such that H is less than the number of edge relaxations, and H+B is less than the number of rows in the matrix. Methodology 900 is initialized by $W_{est}(M,k,0,0)$. The bound obtained by methodology 900 is not greater than the bound derived by methodology 800 since the smaller bound in lines 10-11 is intentionally selected. On the other hand, $W_{est}(M,k,0,0)$ is not less than the optimal value since methodology 900 is just a simulation of the recursion in Equation (4), and in each step, has a greater value.

Therefore, the following conclusion can be drawn: For two non-negative integers H and B in methodology 900, if H≤k and H+B≤n, wherein k is the number of edge relaxations and n is the number of rows in the edge-feature matrix M, then, $$W_{opt}(M,k) \le W_{est}(M,k,0,0) \le W_{apx}(M,k). \quad (5)$$

For a query Q and the maximum allowed selection and disqualifying steps, H and B, the cost of computing $W_{est}$ is irrelevant to the number of the graphs in a database. Thus, the cost of feature miss estimation remains constant with respect to the database size.

Frequency differences will now be described. Assume that $f_1, f_2, \ldots$ and $f_n$ form a feature set used for filtering. Once the upper bound of feature misses is obtained, it can be used to filter graphs in the framework. For a target graph G and a query graph Q, $U=[u_1, u_2, \ldots, u_n]^T$ and $v=[v_1, v_2, \ldots, v_n]^T$ may be their corresponding feature vectors, where $u_i$ and $v_i$ are the frequency (i.e., the number of embeddings) of feature $f_i$ in graphs G and Q.

FIGS. 10A-B are diagrams illustrating exemplary feature vectors. Specifically, FIG. 10A is a diagram illustrating exemplary feature vector u for target graph G and FIG. 10B is a diagram illustrating exemplary feature vector v for query graph Q. As mentioned above, for any feature set, the corresponding feature vector of a target graph can be obtained from the feature-graph matrix index directly without scanning the graph database.

It may then be determined how many more embeddings feature $f_i$ has in the query graph than that in the target graph. Equation (6), below, calculates this frequency difference for feature $f_i$, $$r(u_i, v_i) = \begin{cases} 0, & \text{if } u_i \geq v_i, \\ v_i - u_i, & \text{otherwise} \end{cases} \quad (6)$$

For the feature vectors shown in FIGS. 10A-B, $r(u_1,v_1)=0$. The extra embeddings from the target graph are not taken into account. The summed frequency difference of each feature in G and Q is written as d(G,Q). Equation (7), $$d(G, Q) = \sum_{i=1}^{n} r(u_i, v_i), \quad (7)$$

sums up all the frequency differences.

Suppose the query can be relaxed with k edges. Methodology 900 (FIG. 9) estimates the upper bound of allowed feature misses. If d(G,Q) is greater than that bound, it can be concluded that G does not contain Q within k edge relaxations. For this case, complicated structural comparison between G and Q do not need to be performed. Since all the computations are done on the pre-processed information in the indices, the filtering is actually very fast.

(III) Feature Set Selection

As described, for example, in step 104 of FIG. 1, above, a multi-filter approach may be used to group features with similar selectivity and/or size. The concept of selecting distinct feature sets to form multiple filters to enhance the filtering power will be discussed in this section. In section (II), the basic filtering framework and bounding technique was described. For a given feature set, the performance could not be improved further unless a tighter bound of allowed feature misses is used. Nevertheless, the opportunities of composing filters based on different feature sets can be explored. An interesting question is, should all the features be used together in a single filter? Intuitively, such a strategy would improve the performance since all the available information is used. Unfortunately, very different results are observed in reality. Namely, using all the features together in one filter will deteriorate the performance rather than improve it.

This counter-intuitive result is observed universally. In this section, the reason behind this phenomenon is explained and techniques are discussed that solve this issue by separating features with different characteristics to construct multiple filters.

$u=[u_1, u_2, \ldots, u_n]^T$ and $v=[v_1, v_2, \ldots, v_2]^T$ may be the feature vectors built from a target graph G and a query graph Q. It is assumed that $d_{max}$ is the maximum allowed feature misses. The feature space of a candidate graph can then be described as follows, $$r(u_1,v_1)+r(u_2,v_2)+\ldots+r(u_n,v_n) \leq d_{max}. \quad (8)$$

Any graph whose feature vector satisfies the above inequality is a candidate answer for the query graph. P may be the maximum common subgraph of G and Q. Vector $u'=[u_1', u_2', \ldots u_n']^T$ is its feature vector. If G contains Q within the relaxation ratio, P should contain Q within the relaxation ratio, as well, i.e., $$r(u_1',v_1)+r(u_2',v_2)+\ldots+r(u_n',v_n) \leq d_{max}. \quad (9)$$

Since for any feature $f_i$, $u_i \geq u_i'$, $$r(u_i, v_i) \leq r(u_i', v_i) \text{ and}$$

$$\sum_{i=1}^{n} r(u_i v_i) \leq \sum_{i=1}^{n} r(u_i', v_i).$$

The inequality represented by Equation (9) is stronger, e.g., has greater pruning power, than the inequality represented by Equation (8), above. Logically then, Equation (9) should be checked instead of Equation (8). However, P, the maximum common subgraph of G and Q, should not be calculated beforehand, due to the time involved in doing so. As a result, Equation (8) is the only choice available.

Further, it assumed that Equation (9) does not hold for graph P, and furthermore, that there exists a feature $f_i$ such that its frequency in P is too small to make Equation (9) hold. However, Equation (8) can still be made true for graph G, if the misses of $f_i$ are compensated for by adding more occurrences of another feature $f_j$ in G. This phenomena is called feature conjugation. Feature conjugation likely takes place during filtering since filtering does not distinguish the misses of a single feature, but a collective set of features. It is thus apparent that because of feature conjugation, some graphs that do not satisfy the query requirement may fail to be filtered out.

For example, assume that a graph G contains a sample query graph, such as query graph 400 (FIG. 4), with edge $e_3$ relaxed. In this case, G must have one embedding of feature $f_b$ and two embeddings of $f_c$ ($f_b$ and $f_c$ are in FIG. 5). However, G may be slightly changed such that it does not contain $f_b$ but has one more embedding of $f_c$. This is exactly what $G_4$ has in FIG. 6. The feature conjugation takes place when the miss of $f_b$ is compensated for by the addition of one more occurrence of $f_c$. In such a situation, Equation (8) is still satisfied for $G_4$, although Equation (9) is not.

However, if the features in FIG. 5 are divided into two groups, the feature conjugation problem can be, at least partially, solved. Let group A contain features $f_a$ and $f_b$, and group B contain feature $f_c$ only. For any graph containing query graph 400, shown in FIG. 4, with one edge relaxation (e.g., edge $e_1$, $e_2$ or $e_3$), it must have one embedding in Group A. Using this constraint, $G_4$ in FIG. 6 can be dropped since $G_4$ does not have any embedding of $f_a$ or $f_b$.

The above example also implies that the filtering power may be weakened if all the features are deployed in one filter. A feature has filtering power if its frequency in a target graph is less than its frequency in the query graph. Otherwise, it does not help the filtering. Further, a feature that is good for some graphs in a database may not be good for other graphs in the database. Therefore, a set of features that is uniformly good for a large number of graphs is desired. Selectivity, defined below, is used to measure the filtering power of a feature f for all the graphs in a database. Using the feature-graph matrix index, it takes little time to compute selectivity, since accessing the physical database is not needed.

Selectivity may be defined as follows: For a graph database D, a query graph Q, and a feature f the selectivity of f is defined by its average frequency difference within D and Q, written as $\delta_f(D,Q)$. $\delta_f(D,Q)$ is equal to the average of r(u, v), wherein u is a variable denoting the frequency of f in a graph belonging to D, v is the frequency of f in Q and r is defined in Equation (6). To put features with the same filtering power in a single filter, features are grouped with similar selectivity into the same feature set. Three general principals provide guidance on feature set selection. The first principal is that a large number of features should be selected. The second principal is to make sure features cover the query graph uniformly. The third principal is to separate features with different selectivity.

The first principal, e.g., that a large number of features should be selected, is a notable principal. If, for example, only a small number of features are selected, the maximum allowed feature misses may become very close to $\Sigma_{i=1}^{n} v_i$. In that case, the filtering algorithm loses its pruning power. The second principal, to make sure features cover the query graph uniformly, is based on the same intuition as the first principal. If most of the features cover several common edges, then the relaxation of these edges will make the maximum allowed feature misses too large, e.g., too close to the total number of features. By way of example only, if eight edges of a ten edge query are allowed to be missed, the maximum allowed feature misses is too large. The third principal, to separate features with different selectivity, has been examined above.

In some respects, however, these three principals may not always be consistent with one another. For example, if all the features are used in a query, the second principal, to make sure features cover the query graph uniformly, and the third principal, to separate features with different selectivity, will be violated, since sparse graphs such as chemical structures have features concentrated in the graph center.

Further, low selective features (e.g., which are found in 20 percent or more of the graphs in the database) deteriorate the potential filtering power, as compared to highly selective features (e.g., which are found in less than one percent of the graphs in the database), due to frequency conjugation. However, the most highly selective features cannot be used alone because there may not be enough highly selective features in a query.

Since using a single filter with all the features included is not expected to perform well, a multi-filter composition strategy is devised. Specifically, multiple filters are constructed and coupled together, wherein each filter uses a distinct and complimentary feature set. The three principals, presented above, namely selecting a large number of features, making sure features cover the query graph uniformly and separating features with different selectivity, provide general guidance on how to compose the feature set for each of the filters. One task of feature set selection is to make trade-offs among these principals. For example, features may be grouped by size to create feature sets. This simple scheme satisfies the first principal of selecting a large number of features and the second principal of making sure features cover the query graph uniformly. Usually the selectivity of features with varying sizes is different. Thus, it also roughly meets the third principal of separating features with different selectivity.

A simple, yet viable scheme is thus provided. However, one may go a step further by first grouping features having similar sizes, and then clustering the features, based on their selectivity, to form feature sets.

A simple hierarchical agglomerative clustering methodology is devised based on the selectivity of the features. The final clusters produced represent distinct feature sets for the different filters. The hierarchical agglomerative clustering methodology starts at the bottom, where each feature is an individual cluster. See, for example, FIG. 11, described below. At each level, it recursively merges the two closest clusters into a single cluster. The term "closest" refers to the selectivity of the clusters being the closest. Two parameters are associated with each cluster, the average selectivity of the cluster and the number of features associated with the cluster.

The selectivity of two merged clusters is defined by a linear interpolation of the selectivity of each of the two merged clusters, $$\frac{n_1 \delta_1 + n_2 \delta_2}{n_1 + n_2}, \quad (10)$$

wherein $n_1$ and $n_2$ are the number of features in two clusters, and $\delta_1$ and $\delta_2$ are their corresponding selectivity. The features are first sorted according to their selectivity and then clustered hierarchically. It is assumed that $\delta_{f1}(D,Q) \leq \delta_{f2}(D,Q) \leq \delta_{f3}(D,Q) \leq \ldots$, and so on.

FIG. 11 is a diagram illustrating hierarchical clustering tree 1100. As shown in FIG. 11, $f_5$ is first merged with $f_6$. Subsequent to $f_5$ being merged with $f_6$, $f_1$ is merged with $f_2$. Next, $f_4$ is merged with the cluster formed by $f_5$ and $f_6$, if $f_4$ is the closest one to the cluster. Since the clustering is performed in one dimension, it is very efficient to build.

(IV) Methodology Implementation

As mentioned, for example, in step 104 of FIG. 1, above, a multi-filter approach may be used to group features with similar selectivity or sizes. A filtering technique, e.g., a graph similarity filtering technique comprising two components: a base component and a clustering component, both of which apply to the multi-filter composition strategy, will now be described.

The base component generates feature sets by grouping features having the same size and then using them to filter graphs based on the upper bound of allowed feature misses. See above description of feature miss estimation wherein the upper bound of allowed feature misses is derived. The base component first applies the filter using features with one edge, and then applies the filter using features with two edges, and so on. The base component is denoted by term "graph similarity filtering-base."

The clustering component combines the features whose sizes differ at most by one, and groups them by their selectivity. FIG. 12 is a diagram illustrating exemplary methodology 1200 for graph similarity filtering. In FIG. 12, the loop including lines 1-12 of the code is an iterative process that provides a candidate answer set $C_Q$. $F_i$ in line 2 of methodology 1200 represents the set of features with i edges. Lines 2-4 of methodology 1200 form the base component and lines 5-11 of methodology 1200 form the clustering component.

Once the hierarchical clustering is done on features with i edges and i+1 edges, graph similarity filtering is used to divide the clusters into three groups with high selectivity, medium selectivity and low selectivity. A separate filter is constructed based on each group of features. For the hierarchical clusters shown in FIG. 11, graph similarity filtering techniques will be used to group $f_1$, $f_2$ as group 1, $f_3$ as group 2 and $f_4$, $f_5$, $f_6$ as group 3. To deploy the multiple filters, the graph similarity filtering techniques can be performed in a pipeline mode or a parallel mode.

Figure 13:
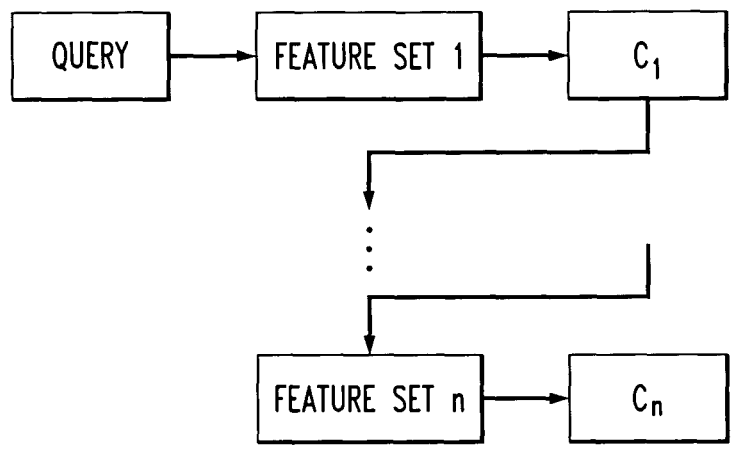
FIG. 13 is a diagram illustrating an exemplary filtering pipeline according to an embodiment of the present invention.

FIG. 13 is a diagram illustrating exemplary filtering pipeline 1300. Specifically, the diagram in FIG. 13 depicts the pipeline mode, wherein the candidate answer set returned from one step is pumped into the next step. Methodology 1200, described, for example, in conjunction with the description of FIG. 12, above, is written in the pipeline mode.

Further, the mode of methodology 1200 can be changed to the parallel mode by replacing line 4 and line 11 of methodology 1200 with the following, $$C_Q = \{G | d(G,Q) \leq d_{max}, G \in D\},$$

and $C_Q$ in line 6 of methodology 1200 with D. With these modifications, graph similarity filtering can be parallelized directly. The final candidate answer set is the intersection of $C_1$, $C_2$, and $C_n$.

There is a slight difference, however, between the pipeline mode and the parallel mode. Graph similarity filtering techniques performed in the pipeline mode can achieve a smaller candidate answer set. The reason is that the clustering component, e.g., line 6 of methodology 1200, in the pipeline mode calculates the selectivity based on the candidate graphs returned in the previous step, while the parallel mode does not. The performance impact raised by this difference is described in section (V), below.

(V) Empirical Study

An examination of the properties of the graph similarity filtering techniques will now be described. The performance of the graph similarity filtering techniques was compared with two alternative methodologies based on a single filter. One methodology used individual edges as features (termed "Edge") and the other methodology used all the features of a query graph (termed "Allfeature"). In fact, the edge-based filtering approach can be viewed as a degenerate case of the feature-based approach using a filter with features of a single edge only. By demonstrating the conditions where the graph similarity filtering techniques can filter more graphs than Edge and Allfeature, it is shown that the present graph similarity filtering techniques can substantially improve substructure similarity searches in large graph databases.

Two kinds of datasets were used in this empirical study. One kind was a real dataset and the other kind was a series of synthetic datasets. The real dataset was an AIDS antiviral screen dataset containing the topological structures of chemical compounds. This dataset is available from the National Cancer Institute/U.S. National Institute of Health (NCI/NIH): Developmental Therapeutics Program (see, e.g., http://dtpsearch.ncifcrf.gov/FTP/AIDO99SD.BIN). In this dataset, thousands of compounds have been checked for evidence of anti-HIV activity. The dataset has around 44,000 structures. A synthetic data generator, which allows a user to specify various parameters, such as the database size, the average graph size, and the label types, e.g., to examine the scalability of the present graph similarity filtering techniques, was employed. The gIndex methodology proposed in Yan, is implemented. Specifically, the gIndex first mines frequent subgraphs having sizes up to ten edges and then retains discriminative edges as indexing features. The discriminative frequent structures are thus taken as the indexing features. Certainly, other kinds of features can be used in the graph similarity filtering techniques also, since the techniques do not rely on the kinds of features used. For example, the present graph similarity filtering techniques can take paths as features to perform the similarity search.

Through experimentation, it is illustrated that the present graph similarity filtering techniques can efficiently prune the search space for substructure similarity searches and outperform the other alternatives up to 15 times in the chemical dataset. It is also illustrated that bound refinement and feature set selection for the multi-filter approach developed by the present graph similarity filtering techniques are both effective. It is further illustrated that the graph similarity filtering techniques perform much better for graphs with a small number of labels. Lastly, it is illustrated that the single filter approach using all features together does not perform well due to the frequency conjugation problem, described, for example, in section (III), above. The approach, also using individual edges as features, does not perform well due to the low selectivity of the edges.

Experiments were also conducted on chemical compound datasets. The performance of the present graph similarity filtering techniques over the AIDS antiviral database is first examined. The test dataset consisted of 10,000 graphs that were randomly selected from the AIDS screen database. These graphs had, on average, about 25 nodes and about 27 edges, with the maximum graph having 214 nodes and 217 edges in total. It is notable that in that dataset, most of the atoms were carbon atoms and most of the edges were carbon-to-carbon bonds. This characteristic made substructure similarity searching very challenging. The query graphs were directly sampled from the database and then grouped together according to their size. The query set was denoted by $Q_m$, where m is the size of the graphs in $Q_m$. For example, if the graphs in a query set had 20 edges each, the query set would be written $Q_{20}$. The edges in the dataset were assigned an edge type, such as single bond, double bond, and so on. By doing so, the number of exact substructure matches were reduced for each query graph. This is exactly the case wherein substructure similarity searching will be very useful, e.g., to find a matching set by relaxing the query graph. Further, when a user submits a substructure similarity query, he or she may not want arbitrary deletion of some critical atoms and/or bonds. In order to simulate this constraint, 25 percent of all the edges in each query graph are retained.

Some slight modifications were made on the Allfeature approach. Namely, features were removed which had sizes greater than the query graph size divided by the number of edge relaxations. This modification improved the performance of Allfeature.

Figure 14:
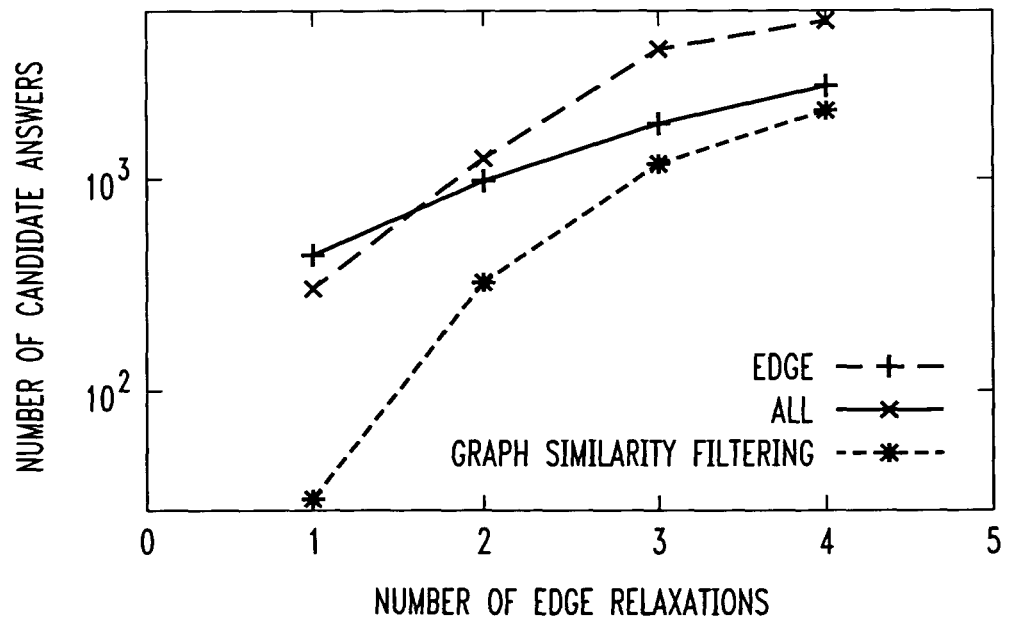
FIG. 14 is a graph illustrating a substructure similarity search of a structure query having 16 edges using several different search methods according to an embodiment of the present invention.

FIG. 14 is a graph illustrating a substructure similarity search of a structure query having 16 edges using several different search methods. Specifically, the graph in FIG. 14 depicts the performance of Edge, Allfeature and the present graph similarity filtering techniques for a structure query with 16 edges (e.g., query set $Q_{16}$). The x-axis shows the number of edge relaxations done for a query graph. The y-axis shows the average number of candidate graphs returned by each search method. As explained above, it is always preferable to filter as many graphs as possible before performing similarity computation. The accurate pair-wise similarity checking is very time-consuming.

If one edge was allowed to be lost for queries having 16 edges, the Edge approach can prune 90 percent of the dataset while the present graph similarity filtering techniques can prune 98 percent. If a user wanted to check whether there are real matches in the remaining two percent of the dataset, he or she can apply the pair-wise similarity computation tools to check them. If the results are not satisfactory, the user can relax the edge loss to 20 percent. The Edge approach will return 18 percent of the dataset and the graph similarity filtering techniques will return 11 percent of the dataset. The running time of the present graph similarity filtering techniques is negligible in comparison with the accurate substructure similarity computation. Using the feature-graph matrix, the filtering stage takes less than one second per query for this query set.

The graph shown in FIG. 14 demonstrates that the present graph similarity filtering techniques outperform Edge and Allfeature significantly when the relaxation ratio is within 13 percent (e.g., 1-2 edges) by a factor of between five and ten times. When the relaxation ratio increases, the performance of the graph similarity filtering techniques becomes closer to Edge. The reason for this is very simple. The structures of chemical compounds are very sparse, and are mainly tree structures with several embedded loops. The term "sparse," as used herein, refers to a graph wherein only a small number of nodes are connected to other nodes. This may be contrasted with "dense" graphs, wherein each node is connected to at least one other node. If three edges were allowed to be deleted or relabeled for a query that has 16 edges, it is likely that the relaxed edges will divide the query graph into four pieces. Each piece may only have four or five edges in total, which most likely will not hold any significant features. Therefore, these small pieces will have, at best, very weak pruning power. Therefore, it is expected that with increases in the relaxation ratio, the present graph similarity filtering techniques will have a performance close to Edge. However, at this time the number of matches will increase dramatically.

Since a user may not want the relaxed query graph to deviate too far from the actual query, he or she may elect a small relaxation ratio. Take the query set $Q_{16}$ as an example. On an average it only has 1.2 exact substructure matches. If two edges are allowed to be relaxed, it will then have 12.8 matches, on an average, which may be enough for examination. This figure is proportional to the number of graphs in the database.

Figure 15:
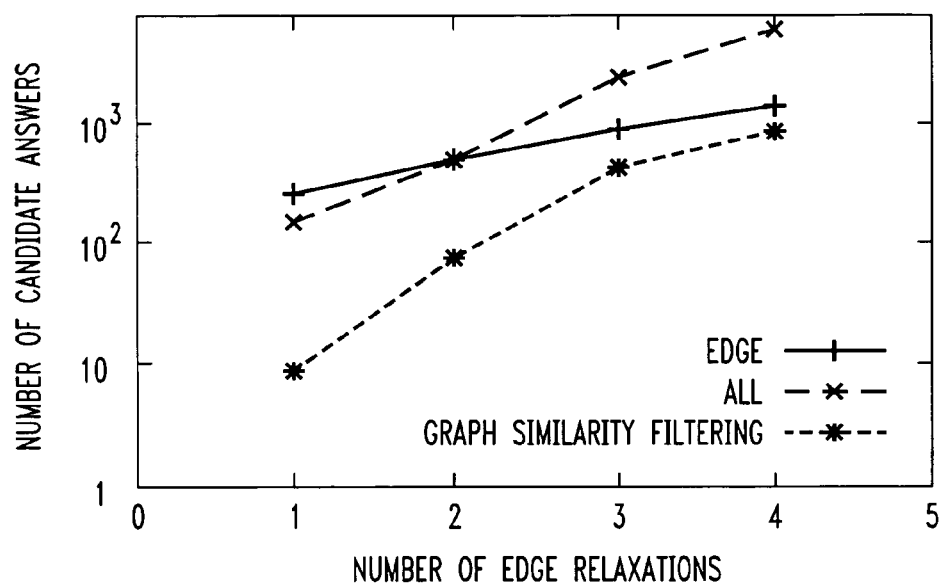
FIG. 15 is a graph illustrating a substructure similarity search of a structure query having 20 edges using several different search methods according to an embodiment of the present invention.

The above result is further confirmed through additional experimentation. Queries having 20 edges are tested. FIG. 15 is a graph illustrating a substructure similarity search of a structure query having 20 edges using several different search methods, namely, graph similarity filtering techniques, Edge and Allfeature. Again, the present graph similarity filtering techniques outperform Edge and Allfeature.

Figure 16:
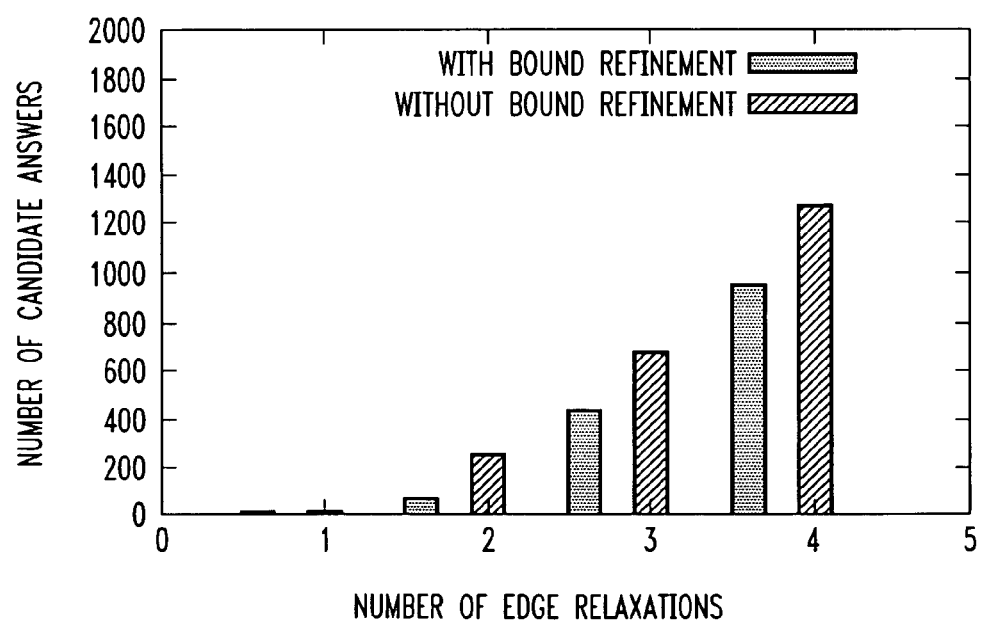
FIG. 16 is a graph illustrating feature miss estimation refinement according to an embodiment of the present invention.

Having examined the overall performance of the graph similarity filtering techniques in comparison with the other two approaches, the effectiveness of each component of graph similarity filtering is now described. $Q_{20}$ is taken as a testing set. FIG. 16 is a graph illustrating feature miss estimation refinement. The graph in FIG. 16 shows the performance differences both before and after the bound refinement is applied to the graph similarity filtering. In this experiment, the maximum number of selection steps (H) is set at two, and the maximum number of disqualifying steps (B) at six. It seems that the bound refinement makes marked improvements when the relaxation ratio is below 20 percent. At high relaxation ratios, bound refinement does not have an apparent effect. As explained above, graph similarity filtering mainly relies on the edge feature set to filter graphs when the ratio is high. In this case, bound refinement will not be effective.

Figure 17:
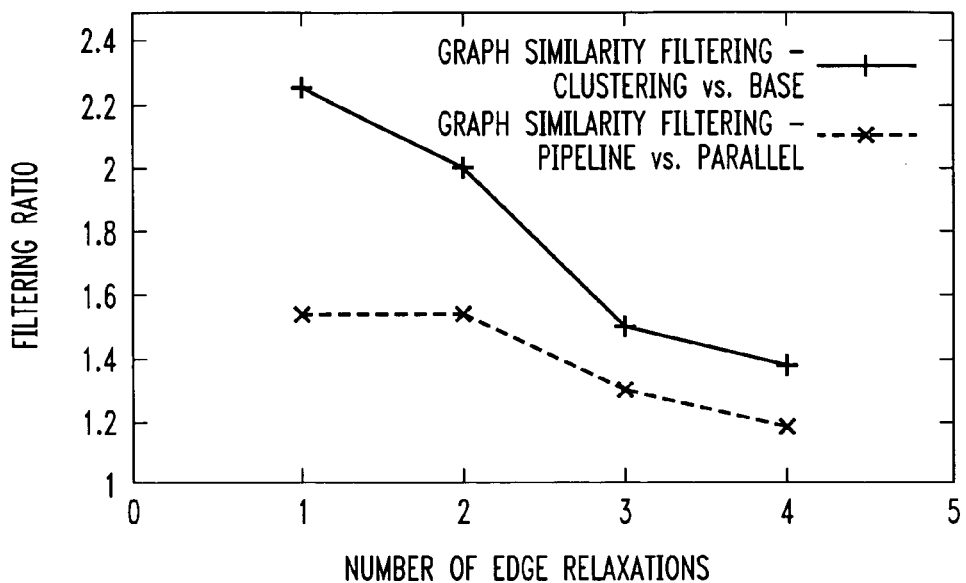
FIG. 17 is a graph illustrating clustering and pipeline improvements according to an embodiment of the present invention.

Thus, bound refinement is worth while for a moderate relaxation ratio. FIG. 17 is a graph illustrating clustering and pipeline improvements. The graph in FIG. 17 shows the filtering ratio obtained by applying the clustering component in graph similarity filtering. $C_Q$ and $C_Q'$ are the candidate answer sets returned by graph similarity filtering (with the clustering component) and the graph similarity filtering-base (with the base component only), respectively. The filtering ratio in FIG. 17 is defined by $$\frac{|C_Q'|}{|C_Q|}.$$

The test is performed on the query set $Q_{20}$. Overall, graph similarity filtering with the clustering component is 40 percent to 120 percent better than graph similarity filtering-base. A similar test was also done to calculate the filtering gain achieved by the pipeline mode over the parallel mode. The pipeline mode was 20 percent to 60 percent better than the parallel mode.

Synthetic datasets were then employed. A synthetic data generator was used to first create a set of structures randomly. The structures created were then randomly combined to form synthesized graphs.

By way of example only, a typical dataset may have 10,000 graphs and use 200 fragments with ten kinds of nodes and edges. This dataset may be denoted by D10kI10T50L200E10V10. E10 means that there are ten kinds of edge labels and V10 means that there are ten kinds of node labels. In this dataset, each graph has 50 edges (e.g., T50) and each fragment has ten edges (e.g., I10) on average.

Since the parameters of synthetic datasets are adjustable, the conditions can be examined wherein graph similarity filtering outperforms Edge. One can imagine that when the types of labels in a graph become very diverse, Edge will perform nearly as well as the present graph similarity filtering techniques. The reason is obvious. Since the graph will have less duplicate edges, it may be treated as a set of tuples {node1_label, node2_label, edge_label} instead of a complex structure.

This result is confirmed by the following experiment. A synthetic dataset, D10kI10T50L200E10V10, was generated which had ten edge labels and ten node labels. This setting generated 10×10×10=1,000 different edge-tuples. Most graphs in this synthetic dataset had 30 to 100 edges. If a graph is represented as a set of edge-tuples, few edge tuples will be the same for each graph in the dataset. In this situation, Edge is good enough for similarity search.

Figure 18:
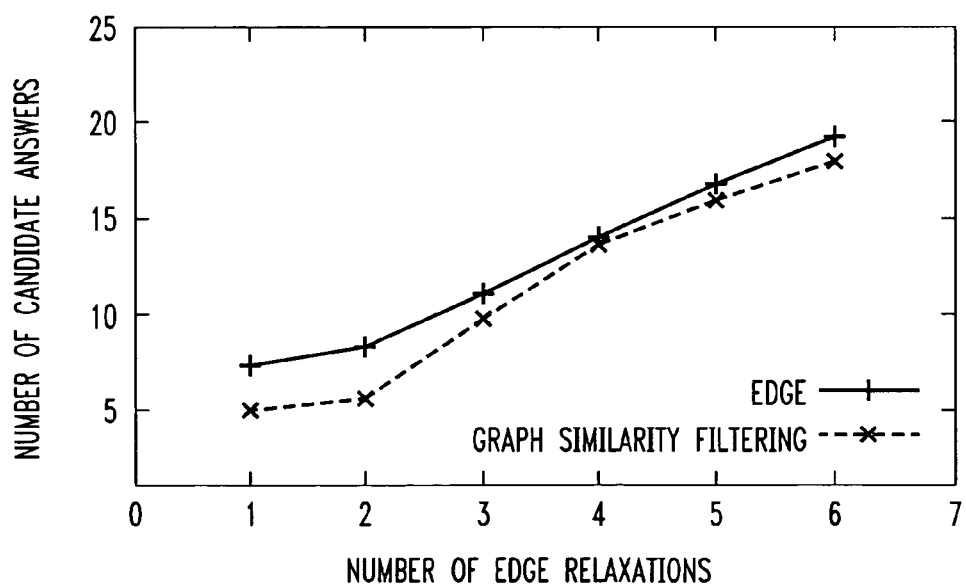
FIG. 18 is a graph illustrating a substructure similarity search using different search methods and employing numerous types of edge labels according to an embodiment of the present invention.

FIG. 18 is a graph illustrating a substructure similarity search using different search methods and employing numerous types of edge labels. Specifically, the graph in FIG. 18 shows the results for graph queries having 24 edges. The curves for Edge and the present graph similarity filtering techniques are very close to each other, which is expected.

Figure 19:
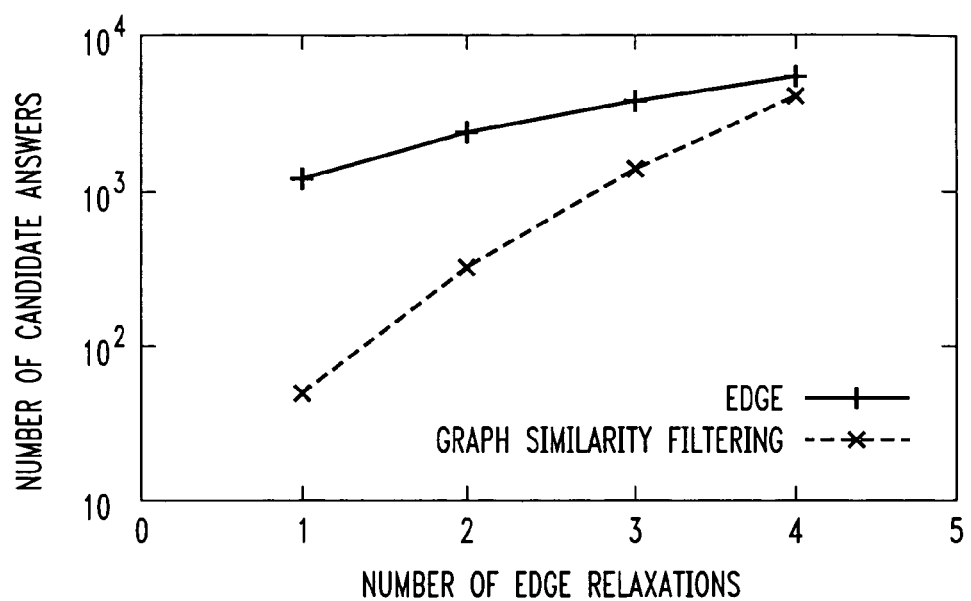
FIG. 19 is a graph illustrating a substructure similarity search using different search methods and employing several types of edge labels according to an embodiment of the present invention.

The number of label types is then reduced in the above synthetic dataset, e.g., allowing only two edge labels and four vertex labels. The results are shown in FIG. 19. FIG. 19 is a graph illustrating a substructure similarity search using different search methods and employing several types of edge labels. This setting significantly increases the self similarity in a graph. The graph in FIG. 19 shows that graph similarity filtering outperforms Edge in this dataset.

The number of label types can be further reduced. For example, if the label information is ignored and only the topological skeleton of graphs are considered, the edge-based filtering algorithm will not be effective at all. In that situation, graph similarity filtering has more advantages than Edge.

Figure 20:
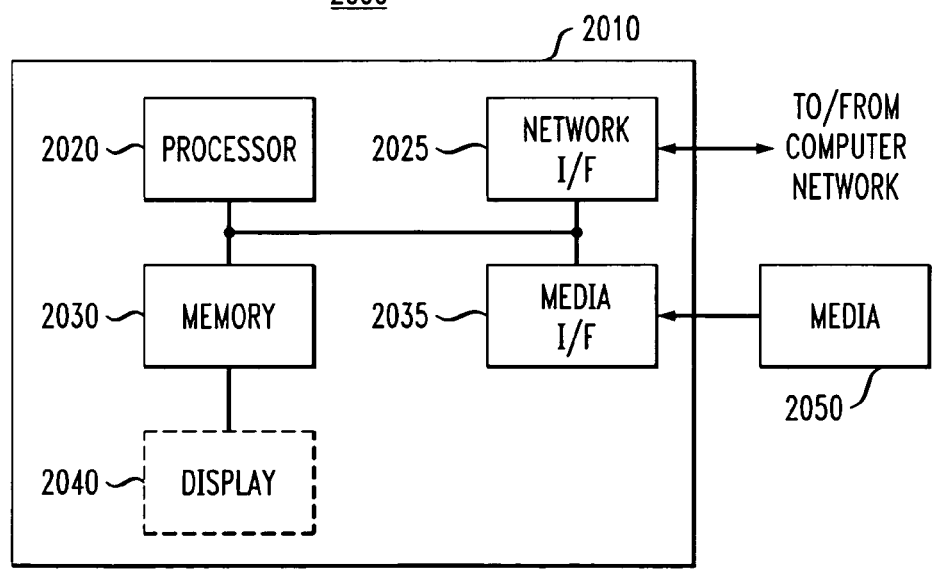
FIG. 20 is a block diagram of an exemplary hardware implementation of one or more of the methodologies of the present invention according to an embodiment of the present invention.

FIG. 20 is a block diagram of an exemplary hardware implementation of one or more of the methodologies of the present invention. Apparatus 2000 comprises a computer system 2010 that interacts with media 2050. Computer system 2010 comprises a processor 2020, a network interface 2025, a memory 2030, a media interface 2035 and an optional display 2040. Network interface 2025 allows computer system 2010 to connect to a network, while media interface 2035 allows computer system 2010 to interact with media 2050, such as a Digital Versatile Disk (DVD) or a hard drive.

As is known in the art, the methods and apparatus discussed herein may be distributed as an article of manufacture that itself comprises a computer-readable medium having computer-readable code means embodied thereon. The computer-readable program code means is operable, in conjunction with a computer system such as computer system 2010, to carry out all or some of the steps to perform one or more of the methods or create the apparatus discussed herein. For example, the computer-readable code is configured to implement a method of searching structural data in a database against one or more structural queries, by the steps of: specifying a desired minimum degree of similarity between the one or more queries and the structural data in the database; and using one or more indices to exclude from consideration any structural data in the database that does not share the minimum degree of similarity with one or more of the queries. The computer-readable medium may be a recordable medium (e.g., floppy disks, hard drive, optical disks such as a DVD, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk.

Memory 2030 configures the processor 2020 to implement the methods, steps, and functions disclosed herein. The memory 2030 could be distributed or local and the processor 2020 could be distributed or singular. The memory 2030 could be implemented as an electrical, magnetic or optical memory, or any combination of these or other types of storage devices. Moreover, the term "memory" should be construed broadly enough to encompass any information able to be read from or written to an address in the addressable space accessed by processor 2020. With this definition, information on a network, accessible through network interface 2025, is still within memory 2030 because the processor 2020 can retrieve the information from the network. It should be noted that each distributed processor that makes up processor 2020 generally contains its own addressable memory space. It should also be noted that some or all of computer system 2010 can be incorporated into an application-specific or general-use integrated circuit.

Optional video display 2040 is any type of video display suitable for interacting with a human user of apparatus 2000. Generally, video display 2040 is a computer monitor or other similar video display.

In conclusion, the present techniques address filtering methodologies using indexed structural patterns, without doing any time prohibitive structural comparisons. The successful transformation of the structure-based similarity measure to the feature-based measure can render the present techniques attractive both in terms of accuracy and efficiency. The present filtering methodologies are built, e.g., on the feature-graph matrix index, and thus perform very fast without accessing the physical database. The multi-filter composition strategy, for example, as may be used in the present graph similarity filtering techniques, proves to be far superior to single filter approaches using all features together, due to the frequency conjugation problem identified above. The direct usage of clustering techniques in feature set selection has also been shown to increase the filtering performance further. Moreover, the graph similarity filtering techniques, disclosed herein, can be directly applied to searching inexact non-consecutive sequences, trees, and other complicated structures as well.

Although illustrative embodiments of the present invention have been described herein, it is to be understood that the invention is not limited to those precise embodiments, and that various other changes and modifications may be made by one skilled in the art without departing from the scope or spirit of the invention.

What is claimed is:

1. A method of searching structural data in a database against one or more structural queries, the method comprising the steps of:
    specifying a desired minimum degree of similarity between the one or more structural queries and the structural data in the database, wherein each of said one or more structural queries is based on a structural representation of a graph;
    using a feature-graph matrix index and an edge-feature matrix index to exclude from consideration any structural data in the database that does not share the desired minimum degree of similarity with one or more of the structural queries based on said structural representation of said graph, wherein each entry of the feature-graph matrix index indicates a number of embeddings of a given feature in a given graph in the database to represent differences between a number of the one or more features present in the one or more structural queries based on said structural representation of said graph and a number of the one or more features present in the structural data in the database, and wherein the edge-feature matrix maps edges and features of the one or more structural queries and represents a limit on a minimum number of features in common between the one or more structural queries based on said structural representation of said graph and the structural data in the database based on a relaxation ratio of the one or more structural queries based on said structural representation of said graph, wherein said relaxation ratio is based on a maximum common subgraph between at least one of said structural queries and the structural data in the database, wherein said graph comprises said structural data comprising one or more features and wherein said one or more features comprise structures indexed in said structural data; and
    identifying the structural data in the database that shares the desired minimum degree of similarity with the one or more of the structural queries based on said structural representation of said graph.

2. The method of claim 1, further comprising searching graphs in the database against one or more query graphs,
    wherein the specifying step further comprises specifying the desired minimum degree of similarity between the one or more query graphs and the graphs in the database, and
    wherein the using step further comprises using the one or more indices to exclude from consideration any graphs in the database that do not share the minimum degree of similarity with the one or more query graphs.

3. The method of claim 1, further comprising the step of identifying structural data in the database that shares at least the desired minimum degree of similarity with at least a portion of one or more of the queries.

4. The method of claim 1, wherein the step of specifying the desired minimum degree of similarity between the one or more queries and the structural data in the database further comprises specifying the desired minimum degree of similarity between the one or more queries and the structural data in the database based on one or more features present in the one or more queries and the structural data in the database.

5. The method of claim 4, wherein the using step further comprises the step of grouping features with similar selectivity to exclude from consideration any structural data in the database that does not share the desired minimum degree of similarity with one or more of the queries, to devise multiple filters using different feature sets.

6. The method of claim 4, wherein the using step further comprises the step of grouping features with similar selectivity to exclude from consideration any structural data in the database that does not share the desired minimum degree of similarity with one or more of the queries, to devise multiple filters using different feature sets, the multiple filters being coupled to each other in one or more of a pipeline and a parallel configuration.

7. The method of claim 4, wherein the using step further comprises the step of grouping features with similar sizes to exclude from consideration any structural data in the database that does not share the desired minimum degree of similarity with one or more of the queries, to devise multiple filters using different feature sets.

8. The method of claim 1, further comprising the steps of:
associating one or more edges present in the structural data in the database and in one or more of the queries with one or more features; and
specifying the desired minimum degree of similarity between the queries and the structural data in the database based on the one or more features.

9. The method of claim 1, wherein the step of specifying the desired minimum degree of similarity between the one or more queries and the structural data in the database further comprises specifying the desired minimum degree of similarity between the one or more queries and the structural data in the database based on one or more features present in one or more of the queries and the structural data in the database, the one or more features comprising one or more of structures indexed in structural databases, paths, edges, discriminative frequent substructures and elementary substructures.

10. The method of claim 1, further comprising the step of altering the desired minimum degree of similarity between the one or more queries and the structural data in the database.

11. The method of claim 1, further comprising the step of relaxing the desired minimum degree of similarity between the one or more queries and the structural data in the database.

12. An apparatus for searching structural data in a database against one or more structural queries, the apparatus comprising:
a memory for storing one or more instructions; and
at least one processor, wherein the one or more instructions are executed by said at least one processor to:
specify a desired minimum degree of similarity between the one or more structural queries and the structural data in the database, wherein each of said one or more structural queries is based on a structural representation of a graph;
use a feature-graph matrix index and an edge-feature matrix index to exclude from consideration any structural data in the database that does not share the desired minimum degree of similarity with one or more of the structural queries based on said structural representation of said graph, wherein each entry of the feature-graph matrix index indicates a number of embeddings of a given feature in a given graph in the database to represent differences between a number of the one or more features present in the one or more structural queries based on said structural representation of said graph and a number of the one or more features present in the structural data in the database, and wherein the edge-feature matrix maps edges and features of the one or more structural queries and represents a limit on a minimum number of features in common between the one or more structural queries based on said structural representation of said graph and the structural data in the database based on a relaxation ratio of the one or more structural queries based on said structural representation of said graph, wherein said relaxation ratio is based on a maximum common subgraph between at least one of said structural queries and the structural data in the database, wherein said graph comprises said structural data comprising one or more features and wherein said one or more features comprise structures indexed in said structural data; and
identify the structural data in the database that shares the desired minimum degree of similarity with the one or more of the structural queries based on said structural representation of said graph.

13. The apparatus of claim 12, wherein said at least one processor is further configured to search graphs in the database against one or more query graphs,
wherein the specifying step further comprises specifying the desired minimum degree of similarity between the one or more query graphs and the graphs in the database, and
wherein the using step further comprises using the one or more indices to exclude from consideration any graphs in the database that do not share the minimum degree of similarity with the one or more query graphs.

14. The apparatus of claim 12, wherein said at least one processor is further configured to identify structural data in the database that shares at least the desired minimum degree of similarity with at least a portion of one or more of the queries.

15. The apparatus of claim 12, wherein the desired minimum degree of similarity between the one or more queries and the structural data in the database further specifies the desired minimum degree of similarity between the one or more queries and the structural data in the database based on one or more features present in the one or more queries and the structural data in the database.

16. The apparatus of claim 12, wherein said at least one processor is further configured to:
associate one or more edges present in the structural data in the database and in one or more of the queries with one or more features; and
specify the desired minimum degree of similarity between the queries and the structural data in the database based on the one or more features.

17. The apparatus of claim 12, wherein the desired minimum degree of similarity between the one or more queries and the structural data in the database further specifies the desired minimum degree of similarity between the one or more queries and the structural data in the database based on one or more features present in one or more of the queries and the structural data in the database, the one or more features comprising one or more of structures indexed in structural databases, paths, edges, discriminative frequent substructures and elementary substructures.

18. The apparatus of claim 12, further comprising the step of altering the desired minimum degree of similarity between the one or more queries and the structural data in the database.

19. The apparatus of claim 12, further comprising the step of relaxing the desired minimum degree of similarity between the one or more queries and the structural data in the database.

20. An article of manufacture for searching structural data in a database against one or more structural queries, comprising a non-transitory machine readable recordable storage medium containing one or more programs which when executed implement the steps of:
specifying a desired minimum degree of similarity between the one or more structural queries and the structural data in the database, wherein each of said one or more structural queries is based on a structural representation of a graph;

using a feature-graph matrix index and an edge-feature matrix index to exclude from consideration any structural data in the database that does not share the desired minimum degree of similarity with one or more of the structural queries based on said structural representation of said graph, wherein each entry of the feature-graph matrix index indicates a number of embeddings of a given feature in a given graph in the database to represent differences between a number of the one or more features present in the one or more structural queries based on said structural representation of said graph and a number of the one or more features present in the structural data in the database, and wherein the edge-feature matrix maps edges and features of the one or more structural queries and represents a limit on a minimum number of features in common between the one or more structural queries based on said structural representation of said graph and the structural data in the database based on a relaxation ratio of the one or more structural queries based on said structural representation of said graph, wherein said relaxation ratio is based on a maximum common subgraph between at least one of said structural queries and the structural data in the database, wherein said graph comprises said structural data comprising one or more features and wherein said one or more features comprise structures indexed in said structural data; and identifying the structural data in the database that shares the desired minimum degree of similarity with the one or more of the structural queries based on said structural representation of said graph.

\* \* \* \* \*